United States Patent [19]

Rajagopalan

[11] Patent Number: 5,321,023

[45] Date of Patent: Jun. 14, 1994

[54] PYRIDOINDOLOBENZODIAZEPINES AND DERIVATIVES AS ANTIPSYCHOTICS

[75] Inventor: Parthasarathi Rajagopalan, Wilmington, Del.

[73] Assignee: The Du Pont Merck Pharmaceutical Co., Wilmington, Del.

[21] Appl. No.: 921,051

[22] Filed: Jul. 29, 1992

[51] Int. Cl.$^5$ ................ C07D 471/14; A61K 31/55
[52] U.S. Cl. ..................................... 514/219; 540/492
[58] Field of Search .................... 514/219; 540/492

[56] References Cited

U.S. PATENT DOCUMENTS

| | | | |
|---|---|---|---|
| 3,373,168 | 3/1968 | Cohen et al. | 260/293 |
| 3,457,271 | 7/1969 | Cohen et al. | 260/296 |
| 3,764,684 | 10/1973 | Finizio | 424/263 |
| 3,790,675 | 2/1974 | Blumberg | 424/263 |
| 3,890,327 | 6/1975 | Berger | 260/295.55 |
| 3,932,650 | 1/1976 | Adams | 424/267 |
| 3,983,123 | 9/1976 | Adams | 260/293.55 |
| 4,018,930 | 4/1977 | Berger | 424/267 |
| 4,438,120 | 3/1984 | Rajagopalan | 260/239.3 |

OTHER PUBLICATIONS

Linnell and Perkin, J. Chem. Soc., 1924, 2451-2459.

Primary Examiner—John M. Ford
Attorney, Agent, or Firm—Gerald J. Boudreaux

[57] ABSTRACT

This invention provides pyrido[4',3':2:3]indolo-[1,7-ab][1,5]benzodiazepines, pharmaceutical compositions containing these compounds, and methods of using these compounds to treat physiological or drug induced psychosis and/or dyskinesia.

18 Claims, No Drawings

PYRIDOINDOLOBENZODIAZEPINES AND DERIVATIVES AS ANTIPSYCHOTICS

FIELD OF THE INVENTION

This invention relates to pyrido[4′,3′:2:3]indolo-[1,7-ab][1,5]benzodiazepines, pharmaceutical compositions containing them, and methods of using these compounds to treat physiological or drug induced psychosis and/or dyskinesia.

BACKGROUND OF THE INVENTION

P. Rajagopalan, U.S. Pat. No. 4,438,120, describes 1,2,3,4,8,9-hexahydropyrido[4′,3′:2,3]-indolo[1,7-ab][1,4]benzodiazepines and 1,2,3,4,4a,8,9,14a-octahydropyrido[4,3,:2,3]indolo[1,7-ab][1,4]benzodiazepines useful as tranquilizers.

Cohen, et al., U.S. Pat. Nos. 3,373,168 and 3,457,271, describe 1,2,3,4,8,9-hexahydropyrido [4′,3′:2,3]indolo[1,7-ab][1]benzazepines and 1,2,3,4,4a,8,9,14a-octahydropyrido[4′,3′:2,3]indolo[1,7-ab][1]benzazepines useful as antidepressants.

Adams, U.S. Pat. Nos. 3,932,650 and 3,983,123, describes 1,2,3,4,4a,8,9,14a-octahydropyrido [4′,3′:2,3]indolo[1,7-ab][1]benzazepines useful as CNS depressants and analgesics.

Berger, U.S. Pat. Nos. 3,890,327 and 4,018,930, describes trans-1,2,3,4,4a,8,9,14a-octahydropyrido [4′,3′:2,3]indolo[1,7-ab][1]benzazepine and its 3-substituted derivatives useful as sedative/tranquilizers.

Blumberg, U.S. Pat. No. 3,790,675, and Finizio, U.S. Pat. No. 3,764,684, describe 1,2,3,4,8,9-hexahydropyrido[4′,3′:2,3]indolo[1,7-ab][1]benzazepines useful as analgesics, anxiolytics and antipsychotics.

W.H. Linnell and W.H. Perkin, Jr., J. Chem. Soc. 1924, 2451 describe the preparations of 1,2,3,4,8,9-hexahydrocarbazolo[1,8-ab][1,4,]benzodiozepin-8(oH)-one.

Traditional neuroleptic antipsychotic drugs include butyrophenones, phenothiazines, thioxanthenes, and diphenylbutylpiperidines. These traditional drugs suffer from the disadvantage of causing neurologic side effects, e.g., extrapyramidal symptoms and tardive dyskinesia, in humans at therapeutically effective doses.

An objective of the present invention is to provide therapeutically effective antipsychotic drugs with reduced neurologic side effects. The present invention provides antipsychotic agents that are structurally dissimilar to traditional neuroleptic antipsychotic drugs. Based on the structural differences between compounds of the present invention and traditional neuroleptic antipsychotic drugs such as haloperidol and chlorpromazine, compounds of the present invention are expected to have a reduced propensity to induce neurologic side effects in humans at therapeutic doses.

SUMMARY OF THE INVENTION

According to the present invention there is provided a compound of formula:

(I)

or a pharmaceutically acceptable salt thereof, wherein:
R is H, alkyl of 1–10 carbon atoms, cycloalkyl of 3–7 carbon atoms, $(CH_2)_nCOR^6$, $(CH_2)_nCH(OH)R^8$; $(CH_2)_nCONR^9R^{10}$, $(CH_2)_n$(cycloalkyl of 3–7 carbon atoms), $(CH_2)_n$-adamantyl, $(CH_2)_nN(R^{15})_2$ or $(CH_2)_n$-W-Ar;

$R^1$, $R^2$, $R^4$, and $R^5$ independently are selected from the group H, alkyl of 1–3 carbon atoms, $CF_3$, Cl, F, Br, OH, $S(O)pR^{14}$, CN or $OCH_3$;

$R^3$ is H, alkyl of 1–3 carbon atoms, cycloalkyl, cycloalkylalkyl, aralkyl or heteroarylalkyl, $COOCH_3$ or $COOC_2H_5$;

$R^6$ is H, OH, $OR^7$, alkyl of 1–6 carbon atoms, cycloalkyl of 3–6 carbon atoms or $(CH_2)_m$—⌬—$R^{12}$ ;

$R^7$ is $CH_3$ or $C_2H_5$;
$R^8$ is H, alkyl of 1–3 carbon atoms, cyloalkyl of 3–6 carbon atoms or $(CH_2)_m$—⌬—$R^{12}$ ;

$R^9$ and $R^{10}$ independently are selected from the group H, $CH_3$, $C_2H_5$, or $R^9$ and $R^{10}$ together are $-(CH_2)_{4-6}-$, $-(CH_2)-O-(CH_2)_2-$, $(CH_2)_2-S-(CH_2)_2-$ or $-(CH_2)_2N(R^7)(CH_2)_2-$;

Ar is aryl substituted with 0–3 $R^{12}$ or heteroaryl substituted with 0–3 $R^{12}$;

$R^{12}$ is independently selected at each occurrence from the group alkyl of 1–3 carbon atoms, phenyl, halogen, alkoxy, CN, $NO_2$, $COR^{13}$, $CO_2R^{13}$, $NR^{13}R^{14}$, and $S(O)pR^{14}$;

$R^{13}$ and $R^{14}$ are each independently selected at each occurrence from the group hydrogen, alkyl of 1–3 carbon atoms and phenyl;

$R^{15}$ is H, alkyl of 1–3 carbon atoms or cycloalkyl of 1–3 carbon atoms;

W is O, S(O)p, or NH;
X is O, S, or 2 H;
n=1–8;
m=0–3; and
p is 0–2.

This invention also provides an intermediate compound, useful for the preparation of compounds of formula (I), having the formula:

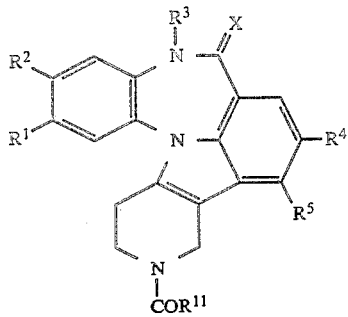

(II)

$R^1$, $R^2$, $R^4$, and $R^5$ independently are selected from the group H, alkyl of 1-3 carbon atoms, $CF_3$, Cl, F, Br, OH, $S(O)pR^{14}$, CN, or $OCH_3$;

$R^3$ is H, alkyl of 1-3 carbon atoms, cycloalkyl, cycloalkylalkyl, aralkyl or heteroarylalkyl, $COOCH_3$ or $COOC_2H_5$;

$R^6$ is H, OH, $OR^7$, alkyl of 1-6 carbon atoms, cycloalkyl of 1-6 carbon atoms or

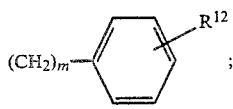

$R^7$ is $CH_3$ or $C_2H_5$;

$R^{11}$ is $CH_3O$, $CH_2H_5O$, $CF_3$, alkyl of 1–9 carbon atoms, $(CH_2)n-1$(cycloalkyl of 3-7 carbon atoms), $(CH_2)n-1$adamantyl, or $(CH_2)n-1$-W-Ar;

Ar is aryl substituted with 0-3 $R^{12}$ or heteroaryl substituted with 0-3 $R^{12}$;

$R^{12}$ is independently selected at each occurrence from the group alkyl of 1-3 carbon atoms, phenyl, halogen, alkoxy, CN, $NO_2$, $COR^{13}$, $CO_2R^{13}$, $NR^{13}R^{14}$, and $S(O)pR^{14}$;

$R^{13}$ and $R^{14}$ are each independently selected at each occurrence from the group hydrogen, alkyl of 1-3 carbon atoms and phenyl;

$R^{15}$ is H, alkyl of 1-3 carbon atoms or cycloalkyl of 1-3 carbon atoms;

W is O, $S(O)p$, or NH;

X is O, S, or 2 H;

n = 1-8;

m = 0-3; and p = 0-2.

PREFERRED EMBODIMENTS

Preferred are compounds of formula (I) or pharmaceutically acceptable salts thereof, wherein:

R is H, alkyl of 1 6 carbon atoms, cycloalkyl of 3-7 carbon atoms, $CH_2$-(cycloalkyl of 3-7 carbon atoms), or $(CH_2)_nAr$;

$R^1$and $R^5$ are H;

$R^2$ is H, $CH_3$, Cl, F, or $CF_3$;

$R^3$ is H or alkyl of 1-3 carbon atoms;

$R^4$ is H, $CH_3$, or Cl;

Ar is aryl substituted with 0-3 $R^{12}$;

$R^{12}$ is H, $CH_3$, $OCH_3$, $NO_2$ or halogen;

n = 1-4; and

X = 2H.

More preferred are those preferred compounds of formula (I) or pharmaceutically acceptable salts thereof, wherein:

R is H, $CH_3$, n-hexyl, cyclopropyl, cyclohexylmethyl, phenethyl, 4-fluorobenzyl;

$R^1$and $R^5$ are H;

$R^2$ is H, $CH_3$, Cl, F, or $CF_3$;

$R^3$ is H, or alkyl of 1-3 carbon atoms;

$R^4$ is H, $CH_3$, or Cl; and

X = 2H.

Specifically preferred are the compounds of formula (I) which are:

11-chloro-1,2,3,4,8,9-hexahydro-3,6-dimethyl-pyrido[4',3':2,3]indolo[1,7-ab][1,5]benzodiazepine;

11-chloro-1,2,3,4,8,9-hexahydro-6-methyl-pyrido[4',3':2,3]indolo[1,7-ab][1,5]benzodiazepine;

11-fluoro-1,2,3,4,8,9-hexahydro-3,6,9-trimethyl-pyrido[4',3':2,3]indolo[1,7-ab][1,5]benzodiazepine;

3-cyclohexylmethyl-1,2,3,4,8,9-hexahydro-11-trifluoromethylpyrido[4',3':2,3]indolo[1,7-ab][1,5]benzodiazepine;

11-chloro-1,2,3,4,8,9-hexahydro-3-benzyl-pyrido[4',3':2,3]indolo[1,7-ab][1,5]benzodiazepine.

In the present invention it has been discovered that compounds of formula (I) are useful as agents to treat physiological or drug induced psychosis and/or dyskinesia. Also provided are pharmaceutical compositions containing compounds of formula (I). The present invention also provides methods for the treatment of drug induced psychosis and/or dyskinesia by administering to a host suffering from such drug induced psychosis or dyskinesia a pharmaceutically effective amount of a compound of formula (I).

When any variable occurs more than one time in any constituent in formula (I), or any other formula herein, its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms. As used herein "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like. "Cycloalkyl-alkyl" is intended to include cycloalkyl attached to alkyl. "Halo" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; "carbocyclic" is intended to mean any stable 5- to 7- membered monocyclic or bicyclic or 7- to 14-membered bicyclic or tricyclic carbon ring, any of which may be saturated, partially unsaturated, or aromatic, for example, indanyl or tetrahydronaphthyl (tetralin).

As used herein, "aralkyl" is intended to mean any aryl group bearing an alkyl group. The aralkyl group may be attached at any of its carbon atoms.

As used herein, the term "heteroaryl" or "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 3 heteroatoms selected from the group consisting of N, 0 and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, pyrazinyl, quinazzoyl, phthalazinyl, naphthyridinyl or octahydroisoquinolinyl.

As used herein, "heteroarylalkyl" is intended to mean heteroaryl bearing an alkyl group. The heteroarylalkyl may be attached at any of its atoms.

The term "substituted", as used herein, means that one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues such as carboxylic acids.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

DETAILED DESCRIPTION OF THE INVENTION

The compounds of this invention may be prepared utilizing any of a number of starting materials and methods known to those skilled in the art of organic synthesis. U.S. Pat. No. 4,438,120, which is herein incorporated by reference, discloses starting materials and methods useful in the preparation of the compounds of this invention. Scheme 1 shows a method for the preparation of compounds of formula (I) wherein X is oxygen. Starting materials for the synthesis of compounds of this invention according to Scheme 1 are 10,11-dihydro-5-nitrosodibenzo[be][1,4]diazepin-11(5H)-ones of formula (1). The preparation of compounds of formula (1) is disclosed in U.S. Pat. No. 4,438,120. According to Scheme 1, a compound of formula (1) is reacted with a reducing agent such as zinc in the presence of an acid such as acetic acid, the reduction product then being condensed in situ with a 4-piperidone of formula (2) also present in the reaction mixture to give an intermediate hydrazone. The resulting hydrazone is converted to its hydrochloride salt and heated in an alcohol solvent, such as 2-propanol at a temperature between 80–100° C to give the corresponding compound of formula (4) as its hydrochloride salt. The free base of (4) can be obtained by treating the hydrochloride salt of (4) with a base, such as sodium hydroxide. Compounds of formula (4) are compounds of formula (I) wherein X is oxygen. These may be further purified, if desired, utilizing standard techniques such as recrystallization and chromatography.

SCHEME 1

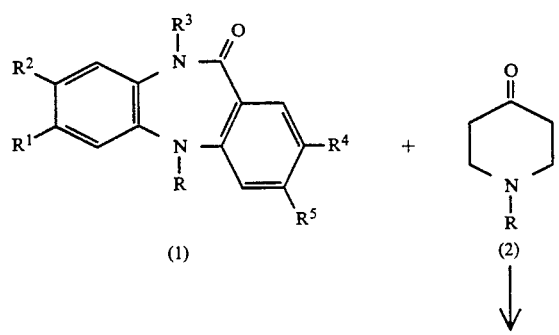

SCHEME 1 -continued

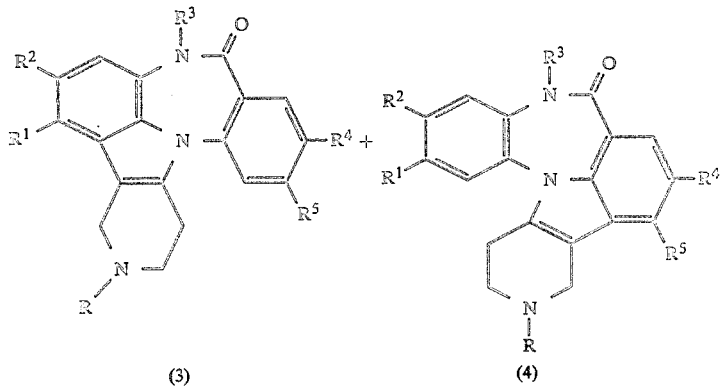

(3)   (4)

A compound of formula (3) may be obtained as a by-product of the reaction of Scheme 1. Compounds of formula (3) are disclosed in U.S. Pat. No. 4,438,120. The proportion of (3) to (4) produced in this reaction may vary according to the substituents $R^1, R^2, R^4$ and $R^5$. The separation of (3) and (4) from the mixture can be effected by exploiting the difference in their solubilities in standard solvents or by high performance liquid chromatography.

In the method of Scheme 1, R of formula (1) cannot be $(CH_2)_nCOR^6$. However, this group can be introduced at a later stage, into compounds of formula (4) where R is H. For example, an R group such as $(CH_2)_nCOR^6$ can be introduced onto the amine nitrogen atom of a compound of formula (4) wherein R is H by alkylation, or by Michael reaction.

A compound of formula (4) (R is H) can be alkylated with an alkyl halide, RX, wherein R is alkyl, such as 1-bromodecane, or $(CH_2)_nCOR^6$ in the presence of a base such as potassium carbonate in a solvent such as dimethyl formamide at a temperature between 50° and 100° C. to yield a compound of formula (4) where R is alkyl or $(CH_2)nCOR^6$.

Additionally, a compound of formula (4) (R is H) can be condensed with an a, b-unsaturated carbonyl compound such as methyl vinyl ketone in a solvent such as dimethylformamide at temperature between 20° and 80° C. to furnish a compound of formula (4) wherein R is $(CH_2)_2COCH_3$.

Additionally, a compound of formula (4) wherein R is not H can be prepared by treating a compound of formula (4) wherein R is H with an acyl halide such as benzoyl chloride in the presence of a base such as triethylamine, in a solvent such as dimethylformamide and at a temperature between 20° to 80° C. to yield a compound of formula (4) wherein R is $COC_6H_5$. This acylated derivative can be reduced to a compound of formula (5) wherein R is benzyl using standard reduction techniques.

Compounds of formula (4) wherein R is $COOR^8$ may be prepared by reaction of compounds of formula (4) wherein R is H with $L-COOR^8$ wherein L is a leaving group such as a halide. Such compounds provide the corresponding compound of formula (5) wherein R is $CH_3$ upon reduction with a suitable reducing agent at a later stage.

A compound of formula (4) wherein R is not H and $R^3$ is H can be alkylated at the 9-position with an alkyl halide, $R^3X$, such as methyl iodide in the presence of a base such as sodium hydride in a solvent such as dimethylformamide at a temperature between 20° and 100° C. to yield a compound of formula (4) wherein $R^3$=methyl.

Compounds of formula (5) can be prepared by reduction of the corresponding compound of formula (4) with a reducing agent such as sodium bis(2-methoxyethoxy)aluminum hydride in a solvent such as benzene at a temperature between 50° and 90° C.

Alternatively, compounds of formula (5) can be prepared by heating a compound of formula (4) with borane in tetrahydrofuran at a temperature between 20° and 80° C., isolating the borane-amine complex formed and heating it with 1-octene in a solvent such as xylene at a temperature between 120°–150° C., followed by standard work-up, isolation and purification procedures.

Compounds of formula (6) wherein R is alkyl, aralkyl, cycloalkyl or cycloalkylalkyl can be prepared from the corresponding compound of formula (4) by heating said corresponding compound with phosphorus pentasulfide in the presence of a solvent such as pyridine or toluene at a temperature between 90° and 100° C.

EXAMPLES

The preparation of compounds provided by this invention is described in detail in the examples which follow. Analytical data were recorded for the compounds described below using the following general procedures. Proton NMR spectra were recorded on a Varian FT-NMR spectrometer (200 MHz or 300 MHz); chemical shifts were recorded in ppm ($\partial$) from an internal tetramethylsilane standard in deuterochloroform or deuterodimethylsulfoxide and coupling constants (J) are reported in Hz. Mass spectra (MS) or high resolution mass spectra (HRMS) were recorded on Finnegan MAT 8230 spectrometer or Hewlett Packard 5988A model spectrometer. Melting points and boiling points are uncorrected.

Reagents were purchased from commercial sources and, where necessary, purified prior to use according to the general procedures outlined by D.D. Perrin and W.L.F. Armarego, Purification of Laboratory Chemicals, 3rd ed., (New York: Pergamon Press, 1988). Chromatography was performed on silica gel using the solvent systems indicated below. For mixed solvent systems, the volume ratios are given. Parts and percentages are by weight unless otherwise specified. Common abbreviations include: THF (tetrahydrofuran), DMF (dimethylformamide), Hz (hertz), TLC (thin layer chromatography).

EXAMPLE 1

11-chloro-1,2,3,4,8,9-hexahydro-3,6-dimethyl-pyrido[4',3':2,3]indolo[1,7-ab][1,5]benzodiazepin-8(9H)-one Acetic acid (1500 ml) was added dropwise to a vigorously stirred mixture of 2-chloro-10,11-dihydro-8-methyl-5-nitrosodibenzo[be][1,4]diazepin-11(5H)-one (92.6 g), 1-methyl-4-piperidone(49.57 g),zinc dust (260 g) and ethanol (1500 ml) maintained at 0° to 5° C. such that the temperature did not rise above 5° C. After the addition was complete the mixture was stirred at room temperature for 2 hours. The residue was washed with a small quantity of ethanol and the combined filtrates were refluxed for 30 minutes and then stripped of ethanol and the excess acetic acid. The residue was treated with water and the solution added to an excess of ammonium hydroxide (28-30%, Ca. 800 ml) with stirring. The mixture was extracted twice with dichloromethane and the combined dichloromethane extracts were washed with water, dried over MgSO$_4$ and stripped of the solvent under reduced pressure to yield a viscous liquid which was dissolved in a minimum quantity of tetrahydrofuran and the solution added to 0.5N solution of hydrogen chloride in anhydrous ether (1000 ml). The salt that separated was filtered off, washed with ether, suspended in 2-propanol (500 ml) and refluxed with stirring overnight. The hot mixture was filtered and the collected solid was washed with 2-propanol, then with ether and boiled again with 2-propanol (200 ml). The hot mixture was filtered and the collected solid was washed with ether and then suspended in 500 ml of 1N NaOH solution and stirred at room temperature for 30 minutes and the mixture then filtered. Alternately, the solid can be suspended in an excess of ammonium hydroxide (28-30%) and the mixture heated with stirring on a steam bath for 30 minutes and filtered. The collected solid was washed with water, pressed dry and boiled with 2-propanol, and the hot mixture filtered. The collected product was washed with a little ether, air-dried and then subjected to three hot triturations with a 3:1 mixture of 2-propanol and methanol to yield 3.1 g 11-chloro-1,2,3,4,8,9-hexahydro-3,6-dimethyl-pyrido [4',3':2,3]indolo[1,7-ab][1,5]benzodiazepin-8(9H)-one, m.p. 264°-267° C. (dec.).

EXAMPLE 23

11-chloro-1,2,3,4,8,9-hexahydro-3,6-dimethyl-pyrido[4',3':2,3]indolo[1,7-ab][1,5]benzodiazepine A solution of sodium bis(2-methoxyethoxy) aluminum hydride in toluene (3M,23 ml) was added, dropwise, to a stirred suspension of 11-chloro-1,2,3,4,8,9-hexahydro-3,6-dimethylpyrido[4',3':2,3]-indolo[1,7-ab]benzodiazepin-8(9H)-one (5.02 g) in benzene (300 ml) under nitrogen. After the addition was complete the mixture was refluxed for 2 hours, cooled to 15°-20° C. stirred and treated with 20% aqueous sodium hydroxide (150 ml) added dropwise initially and rapidly after the excess of the reducing agent had been destroyed. The mixture was transferred to a separatory funnel and shaken vigorously after the addition of water (150 ml). The organic layer was removed and the aqueous layer extracted once with benzene and the combined organic extracts were washed with water, dried over MgSO$_4$ and stripped of the solvent under reduced pressure. The residual foamy solid was boiled briefly with a 4:1 mixture of ethyl acetate and hexanes, cooled and filtered to yield 3.51 g of 11-chloro-1,2,3,4,8,9-hexahydropyrido-3,6-dimethylpyrido[4',3':2,3]indolo[1,7-ab][1,5] benzodiazepine as a crystalline solid, m.p. 182°-184°.

TABLE 1

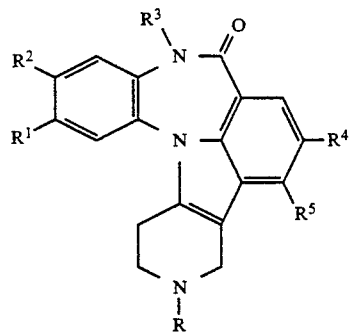

| Ex | R | R$^1$ | R$^2$ | R$^3$ | R$^4$ | R$^5$ | X | M.P. °C. |
|---|---|---|---|---|---|---|---|---|
| 1 | CH$_3$ | H | Cl | H | CH$_3$ | H | O | 264–267 (dec.) |
| 2 | H | H | Cl | H | CH$_2$ | H | O | 295–296 (dec.) |
| 3 | CH$_3$ | H | CF$_3$ | H | CH$_3$ | H | O | 289–290 (dec.) |
| 4 | CH$_3$ | H | H | H | H | H | O | |
| 5 | CH$_3$ | H | Cl | CH$_3$ | CH$_3$ | H | O | |
| 6 | CH$_3$ | H | Cl | H | H | CH$_3$ | O | |
| 7 | CH$_3$ | H | F | H | CH$_3$ | H | O | |
| 8 | CH$_3$ | H | Cl | H | H | H | S | |
| 9 | CH$_3$ | H | H | H | Cl | H | O | |
| 10 | CH$_3$ | H | Cl | H | CH$_3$O | H | O | |
| 11 | CH$_3$ | H | Cl | H | HO | H | O | |
| 12 | CH$_3$ | CH$_3$O | H | H | CH$_3$ | H | O | |
| 13 | n-C$_{10}$H$_{21}$ | H | Cl | H | CH$_3$ | H | O | |
| 14 | C$_6$H$_5$CH$_2$ | H | Cl | H | CH$_3$ | H | O | |

TABLE 1-continued

| Ex. | R | R¹ | R² | R³ | R⁴ | R⁵ | X | M.P. °C. |
|---|---|---|---|---|---|---|---|---|
| 15 | cyclopropyl | H | Cl | H | CH₃ | H | O | |
| 16 | cyclohexyl-CH₂ | H | Cl | H | H | H | O | |
| 17 | Adamantyl-CH₂ | H | Cl | H | CH₃ | H | O | |
| 18 | CH₃CO(CH₂)₂ | H | Cl | H | CH₃ | H | O | |
| 19 | C₆H₅CO(CH₂)₂ | H | Cl | H | CH₃ | H | O | |
| 20 | (CH₂)₃COOC₂H₅ | H | Cl | H | CH₃ | H | O | |
| 21 | (CH2)2CN | H | Cl | H | CH₃ | H | O | |
| 22 | (CH₂)₂CON(CH₃)₂ | H | Cl | H | CH₃ | H | O | |

TABLE 2

(5)  (6)

| Ex. | R | R¹ | R² | R³ | R⁴ | R⁵ | M.P. °C. |
|---|---|---|---|---|---|---|---|
| 23 | CH₃ | H | Cl | H | CH₃ | H | 182–184 |
| 24 | H | H | Cl | H | CH₃ | H | 232–233 |
| 25 | CH₃ | H | CF₃ | H | CH₃ | H | 210–211 |
| 26 | CH₃ | H | H | H | H | H | |
| 27 | CH₃ | H | Cl | CH₃ | CH₃ | H | |
| 28 | CH₃ | H | Cl | H | H | CH₃ | |
| 29 | CH₃ | H | F | H | CH₃ | H | |
| 30 | CH₃ | H | H | H | Cl | H | |
| 31 | CH₃ | H | Cl | H | CH₃O | H | |
| 32 | CH₃ | H | Cl | H | HO | H | |
| 33 | CH₃ | CH₃O | H | H | CH₃ | H | |
| 34 | n-C₁₀H₂₁ | H | Cl | H | CH₃ | H | |
| 35 | C₆H₅CH₂ | H | Cl | H | CH₃ | H | |
| 36 | cyclopropyl | H | Cl | H | CH₃ | H | |
| 37 | cyclohexyl-CH₂ | H | Cl | H | H | H | |

TABLE 2-continued

| # | | R1 | R2 | R3 | R4 | R5 |
|---|---|---|---|---|---|---|
| 38 | Adamantyl-CH$_2$ | H | Cl | H | CH$_3$ | H |
| 39 | F—⟨phenyl⟩—CO(CH$_2$)$_3$ | H | Cl | H | CH$_3$ | H |
| 40 | HO(CH$_2$)$_4$ | H | Cl | H | CH$_3$ | H |
| 41 | (CH$_2$)$_2$COCH$_3$ | H | Cl | CH$_3$ | CH$_3$ | H |
| 42 | (CH$_2$)$_2$CN | H | Cl | CH$_3$ | H | H |

UTILITY SECTION

The compounds of this invention and their pharmaceutically acceptable salts possess psychotropic properties, particularly antipsychotic activity of good duration, while lacking the typical movement disorder side-effects of standard antipsychotic agents. Thus, these compounds may be useful in the treatment of physiological psychosis. These compounds may also be useful as antidotes for certain psychotomimetic agents such as phencyclidine (PCP), and as antidyskinetic agents.

Conditioned Avoidance Responding in Rat

The procedure utilized is a modification of the procedure of Cook and Weidley (Ann. NY Acad Sci.66: 740–752, 1957).

Apparatus: A Coulbourn Instruments large modular test cage (25×30×30 cm) with a pole suspended from the center of the ceiling and a stainless steel grid floor. A 0.75 mA pulsed current (250 msec on, 750 msec off) is delivered to the grid floor by a Coulbourn Instruments programmable shocker.

Animals: Male CDF rats are purchased from Charles River Breeding Laboratories (Wilmington, Mass.).

Test Procedure: Each trial lasts 25 seconds. Ten seconds after the rat is placed in the testing apparatus, footshock is delivered for 15 seconds. The rat is immediately removed from the testing apparatus. If the rat climbs the pole within the first 10 seconds, footshock is avoided and an avoidance response is recorded. If the rat climbs the pole during the footshock period, an escape response is recorded. If the animal fails to climb the pole during the 25 second trial period, an escape failure is recorded.

Drug testing is initiated after rats are well trained to consistently avoid footshock. Rats are tested for conditioned avoidance responding at various time intervals (30–360 minutes) after oral administration of test compound.

For each dose of test compound, inhibition of conditioned avoidance responding is expressed as a percentage of the corresponding Drug Vehicle (control) value. The percent antagonism is used to calculate ED50 values when appropriate.

Results:

| Example # | Peak ED$_{50}$ |
|---|---|
| 1 | +++ |
| 3 | ++ |
| 23 | +++ |
| 25 | +++ |

A Peak ED$_{50}$ value ≦20 mg/kg corresponds to +++; a value between 20–50 mg/kg corresponds to ++; a value between 50–100 corresponds to +; a value >100 corresponds to —.

Induction of Catalepsy

This is a modification of the method of Costall and Naylor (Psychopharmacologia (Berl.), 43, 69–74, 1975). Male CD rats (Charles River) weighing 250–300 grams were treated with test drugs and standards by the oral route and tested for the presence of catalepsy at various time intervals (30–360 minutes) after oral administration of test compound. To test for catalepsy, each rat is placed with its front paws over a 10 cm high horizontal bar. The intensity of catalepsy is measured by the length of time it takes the animal to move both forelegs to the table. A time of 20 seconds is considered maximal catalepsy. This test best predicts the side effects profile (Parkinson-like symptoms, tardive dyskinesia) of a compound. A representative compound of this invention was tested and found to have an ED$_{50}$ (mg/kg PO) value greater than 60 mg/kg one hour post administration. This result indicates that compounds of the present invention should have a reduced propensity to induce neurologic side effects in humans.

These results demonstate that the compounds of the present invention have utility as antipsychotics and as antidyskinetics.

DOSAGE FORMS

Daily dosage ranges from 1 mg to 2000 mg. Dosage forms (compositions) suitable for administration ordinarily will contain 0.5–95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

What is claimed is:

1. A compound having the formula:

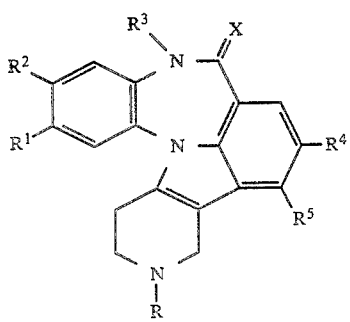
(I)

or a pharmaceutically acceptable salt thereof, wherein:

R is H, alkyl of 1–10 carbon atoms, cycloalkyl of 3–7 carbon atoms, $(CH_2)_nCOR^6$, $(CH_2)_nCH(OH)R^8$; $(CH_2)_nCONR^9R^{10}$, $(CH_2)_n$(cycloalkyl of 3–7 carbon atoms), $(CH_2)_n$-adamantyl, $(CH_2)_nN(R^{15})_2$ or $(CH_2)_n$-W-Ar;

$R^1$, $R^2$, $R^4$, and $R^5$ independently are selected from the group H, alkyl of 1–3 carbon atoms, $CF_3$, Cl, F, Br, OH, $S(O)_pR^{14}$, CN or $OCH_3$;

$R^3$ is H, alkyl of 1–3 carbon atoms, cycloalkyl of 3–8 carbon atoms, cycloalkylalkyl of 4–10 carbon atoms, phenyl ($C_1$–$C_{10}$ alkyl), naphthyl ($C_1$–$C_{10}$ alkyl), or a heterocycle substituted with alkyl of 1–10 carbon atoms selected from the group: pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, pyrazinyl, quinazzoyl, phthalazinyl, naphthyridinyl or octahydroisoquinolinyl, $COOCH_3$ or $COOC_2H_5$;

$R^6$ is H, OH, $OR^7$, alkyl of 1–6 carbon atoms, cycloalkyl of 3–6 carbon atoms or

;

$R^7$ is $CH_3$ or $C_2H_5$;

$R^8$ is H, alkyl of 1–3 carbon atoms, cycloalkyl of 3–6 carbon atoms or

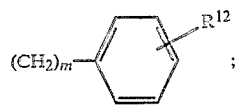;

$R^9$ and $R^{10}$ independently are selected from the group H, $CH_3$, $C_2H_5$, or $R^9$ and $R^{10}$ together are $-(CH_2)_{4-6}-$, $-(CH_2)_2-O-(CH_2)_2-$, $(CH_2)_2-S-(CH_2)_2-$ or $-(CH_2)_2N(R^7)(CH_2)_2-$;

Ar is phenyl or naphthyl substituted with 0–3 $R^{12}$ or a heterocycle selected from the group: pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, pyrazinyl, quinazzoyl, phthalazinyl, naphthyridinyl or octahydrosoisoquinolinyl substituted with 0–3 $R^{12}$;

$R^{12}$ is independently selected at each occurrence from the group alkyl of 1–3 carbon atoms, phenyl, halogen, alkoxy, CN, $NO_2$, $COR^{13}$, $CO_2R^{13}$, $NR^{13}R^{14}$, and $S(O)pR^{14}$;

$R^{13}$ and $R^{14}$ are each independently selected at each occurrence from the group hydrogen, alkyl of 1–3 carbon atoms and phenyl;

$R^{15}$ is H, alkyl of 1–3 carbon atoms or cycloalkyl of 3–6 carbon atoms;

W is O, S(O)p, or NH;

X is S, or 2 H;

n = 1–8;

m = 0–3; and p is 0–2.

2. A compound of claim 1 wherein:

R is H, alkyl of 1–6 carbon atoms, cycloalkyl of 3–7 carbon atoms, $CH_2$-(cycloalkyl of 3–7 carbon atoms), or $(CH_2)_nAr$;

$R^1$ and $R^5$ are H;

$R^2$ is H, $CH_3$, Cl, F, or $CF_3$;

$R^3$ is H or alkyl of 1–3 carbon atoms;

$R^4$ is H, $CH_3$, or Cl;

Ar is phenyl or napthyl substituted with 0–3 $R^{12}$;

$R^{12}$ is H, $CH_3$, $OCH_3$ or $NO_2$;

X is 2H; and n = 1–4.

3. A compound of claim 2 wherein:

R is H, $CH_3$, n-hexyl, cyclopropyl, cyclohexylmethyl, phenethyl, 4-fluorobenzyl;

$R^1$ and $R^5$ are H;

$R^2$ is H, $CH_3$, Cl, F, or $CF_3$;

$R^3$ is H, or alkyl of 1–3 carbon atoms; and $R^4$ is H, $CH_3$, or Cl.

4. The compounds of claim 1 which are
11-chloro-1,2,3,4,8,9-hexahydro-3,6-diamethyl-pyrido[4',3':2,3]indolo[1,7-ab][1,5]benzodiazepine;
11-chloro-1,2,3,4,8,9-hexahydro-6-methyl-pyrido[4',3':2,3]indolo[1,7-ab][1,5]benzodiazepine;
11-fluoro-1,2,3,4,8,9-hexahydro-3,6,9-trimethyl-pyrido[4',3':2,3]indolo[1,7-ab][1,5]benzodiazepine;
3-cyclohexylmethyl-1,2,3,4,8,9-hexahydro-11-trifluoromethylpyrido[4',3':2,3]indolo[1,7-ab][1,5]benzodiazepine;
11-chloro-1,2,3,4,8,9-hexahydro-3-benzyl-pyrido[4',3':2,3]indolo[1,7-ab][1,5]benzodiazepine.

5. The compound of claim 4 which is:

11-chloro-1,2,3,4,8,9-hexahydro-3,6-dimethyl-pyrido[4',3':2,3]indolo[1,7-ab][1,5]benzodiazepine;

6. A pharmaceutical composition comprising a pharmaceutically acceptable carrier and an antipsychotic effective amount of a compound of claim 1.

7. A pharmaceutical composition comprising a pharmaceutically acceptable carrier and an antipsychotic effective amount of a compound of claim 2.

8. A pharmaceutical composition comprising a pharmaceutically acceptable carrier and an antipsychotic effective amount of a compound of claim 3.

9. A pharmaceutical composition comprising a pharmaceutically acceptable carrier and an antipsychotic effective amount of a compound of claim 4.

10. A pharmaceutical composition comprising a pharmaceutically acceptable carrier and an antipsychotic effective amount of the compound of claim 5.

11. A method of treating physiological or drug induced psychosis or dyskinesia in a mammal comprising administering to said mammal an antipsychotic or antidyskinetic effective amount of a compound of claim 1.

12. A method of treating physiological or drug induced psychosis or dyskinesia in a mammal comprising administering to said mammal an antipsychotic or antidyskinetic effective amount of a compound of claim 2.

13. A method of treating physiological or drug induced psychosis or dyskinesia in a mammal comprising administering to said mammal an antipsychotic or antidyskinetic effective amount of a compound of claim 3.

14. A method of treating physiological or drug induced psychosis or dyskinesia in a mammal comprising administering to said mammal an antipsychotic or antidyskinetic effective amount of a compound of claim 4.

15. A method of treating physiological or drug induced psychosis or dyskinesia in a mammal comprising administering to said mammal an antipsychotic or antidyskinetic effective amount of the compound of claim 5.

16. A compound having the formula:

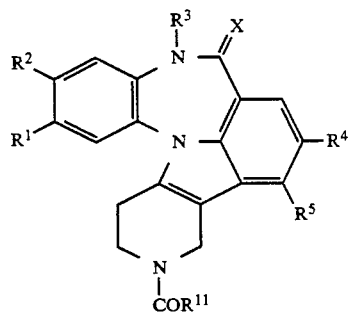

(II)

wherein:

$R^1$, $R^2$, $R^4$, and $R^5$ independently are selected from the group H, alkyl of 1-3 carbon atoms, $CF_3$, Cl, F, Br, OH, or $OCH_3$;

$R^3$ is H, alkyl of 1-3 carbon atoms, cycloalkyl of 3-8 carbon atoms, cycloalkylalkyl of 4-10 carbon atoms, phenyl ($C_1$-$C_{10}$ alkyl), naphthyl ($C_1$-$C_{10}$ alkyl), or a heterocycle substituted with alkyl of 1-10 carbon atoms selected from the group: pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, pyrazinyl, quinazzoyl, phthalazinyl, naphthyridinyl or octahydroisoquinolinyl, $COOCH_3$ or $COOC_2H_5$;

$R^7$ is $CH_3$ or $C_2H_5$;

$R^{11}$ is $CH_3O$, $CH_2H_5O$, alkyl of 1-9 carbon atoms, $(CH_2)n-1$ (cycloalkyl of 3-7 carbon atoms), $(CH_2)n-1$ adamantyl, or $(CH_2)n-1$-W-Ar;

Ar is phenyl or naphthyl substituted with 0-3 $R^{12}$ or a heterocycle selected from the group: pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, pyrazinyl, quinazzoyl, phthalazinyl, naphthyridinyl or octahydrosoisoquinolinyl substituted with 0-3 $R^{12}$;

$R^{12}$ is independently selected at each occurrence from the group alkyl of 1-3 carbon atoms, phenyl, halogen, alkoxy, CN, $NO_2$, $COR^{13}$, $CO_2R^{13}$, $NR^{13}R^{14}$, and $S(O)pR^{14}$;

$R^{13}$ and $R^{14}$ are each independently selected at each occurrence from the group hydrogen, alkyl of 1-3 carbon atoms and phenyl;

W is O, S(O)p, or $CH_2$;

X is S, or 2 H;

n=1-8;

m=0-3; and p is 0-2.

17. The compound of claim 16 wherein:

R is H, alkyl of 1-6 carbon atoms, cycloalkyl of 3-7 carbon atoms, $CH_2$-(cycloalkyl of 3-7 carbon atoms), or $(CH_2)_nAr$;

$R^1$ and $R^5$ are H;

$R^2$ is H, $CH_3$, Cl, F, or $CF_3$;

$R^3$ is H or alkyl of 1-3 carbon atoms;

$R^4$ is H, $CH_3$, or Cl;

Ar is phenyl or naphthyl substituted with 0-3 $R^{12}$;

$R^{12}$ is H, $CH_3$, $OCH_3$ or $NO_2$;

X is 2H; and n=1-4.

18. The compound of claim 17 wherein:

R is H, $CH_3$, n-hexyl, cyclopropyl, cyclohexylmethyl, phenethyl, or 4-fluorobenzyl;

$R^1$ and $R^5$ are H;

$R^2$ is H, $CH_3$, Cl, F, or $CF_3$;

$R^3$ is H, or alkyl of 1-3 carbon atoms; and $R^4$ is H, $CH_3$, or Cl.

* * * * *